(12) United States Patent
Wang

(10) Patent No.: US 12,011,333 B2
(45) Date of Patent: Jun. 18, 2024

(54) METAL ORTHODONTIC MOUTH GAG

(71) Applicant: THE SECOND AFFILIATED HOSPITAL OF CHONGQING MEDICAL UNIVERSITY, Chongqing (CN)

(72) Inventor: Shengguo Wang, Chongqing (CN)

(73) Assignee: The Second Affiliated Hospital of Chongqing Medical University, Chongqing (CN)

( * ) Notice: Subject to any disclaimer, the term of this patent is extended or adjusted under 35 U.S.C. 154(b) by 241 days.

(21) Appl. No.: 17/595,458

(22) PCT Filed: Jun. 24, 2020

(86) PCT No.: PCT/CN2020/097828
§ 371 (c)(1),
(2) Date: Nov. 17, 2021

(87) PCT Pub. No.: WO2021/042822
PCT Pub. Date: Mar. 11, 2021

(65) Prior Publication Data
US 2022/0192788 A1    Jun. 23, 2022

(30) Foreign Application Priority Data
Sep. 4, 2019  (CN) .......................... 201910832948.6

(51) Int. Cl.
*A61B 1/24*     (2006.01)
*A61C 7/02*     (2006.01)

(52) U.S. Cl.
CPC . *A61C 7/02* (2013.01); *A61B 1/24* (2013.01)

(58) Field of Classification Search
CPC .............. A61B 1/24; A61C 17/10; A61C 7/02
See application file for complete search history.

(56) References Cited

U.S. PATENT DOCUMENTS

| | | | | |
|---|---|---|---|---|
| 3,241,550 A | * | 3/1966 | Gelarie | A61B 1/24 600/242 |
| 4,002,162 A | * | 1/1977 | Weisser | A61B 13/00 600/242 |
| 5,199,872 A | * | 4/1993 | Leal | A61B 1/24 433/136 |
| 5,927,276 A | * | 7/1999 | Rodriguez | A61M 16/0488 128/DIG. 26 |

(Continued)

*Primary Examiner* — Ralph A Lewis
(74) *Attorney, Agent, or Firm* — Natter & Associates, P.C.; Howard Natter

(57) ABSTRACT

A metal orthodontic mouth gag is provided, which includes an upper supporting frame, a lower supporting frame, a supporting wing of a left molar area and a supporting wing of a right molar area. The upper supporting frame is a serpentine upper bent rod which is made by a thin steel wire being sequentially wound up and down, and the lower supporting frame is a serpentine lower bent rod which is made by a thin steel wire being sequentially wound up and down. The supporting wing of the left molar area includes a left C-shaped supporting rod and a left blocking supporting frame, and the supporting wing of the right molar area includes a right C-shaped supporting rod and a right blocking supporting frame. The blocking supporting frames are connected into the corresponding C-shaped supporting rods.

12 Claims, 3 Drawing Sheets

(56) References Cited

U.S. PATENT DOCUMENTS

| | | | | |
|---|---|---|---|---|
| 7,077,652 B2 * | 7/2006 | Kilcher | ............... | A61C 5/90 |
| | | | | 433/136 |
| 7,300,401 B2 * | 11/2007 | Patrickus | ............. | A61C 17/10 |
| | | | | 600/242 |
| 8,376,743 B1 * | 2/2013 | Bukhary | ............. | A61C 5/90 |
| | | | | 600/209 |
| 2002/0087051 A1 * | 7/2002 | Levisman | ............ | A61B 1/24 |
| | | | | 600/209 |
| 2005/0171406 A1 * | 8/2005 | Dorfman | ............. | A61B 1/24 |
| | | | | 600/237 |
| 2005/0227199 A1 * | 10/2005 | Patrickus | ............. | A61C 17/10 |
| | | | | 433/93 |
| 2006/0063979 A1 * | 3/2006 | Rosenblood | ......... | A61B 1/24 |
| | | | | 600/237 |

* cited by examiner

US 12,011,333 B2

METAL ORTHODONTIC MOUTH GAG

CROSS REFERENCE TO RELATED APPLICATION

This patent application is a national phase application of International Patent Application No. PCT/CN2020/097828, filed on Jun. 24, 2020, which claims priority to Chinese Patent Application No. 201910832948.6 filed on Sep. 4, 2019, the entire content of each of which is incorporated herein by reference.

TECHNICAL FIELD

The present disclosure relates to a medical instrument for oral use, and in particular, to a metal orthodontic mouth gag.

BACKGROUND ART

In orthodontic clinical operation for the oral cavity, a mouth gag is a common auxiliary tool for bonding a bracket. In order to achieve the best correction effect, it is often necessary to bond orthodontic attachments to a second permanent molar and even to a third molar.

At present, the application of a band has the problems of difficulty in positioning and accurate positioning. Meanwhile, the application of the band is more irritating to the buccal mucosa, and the food impaction occurs easily after correction. For this reason, Chinese patents (Authorized Publication Numbers are CN 103919621 B and CN 103876852 B) both optimize the structure of the mouth gag, that is, the buccal mucosa of a molar area can be supported while the buccal mucosa of a front lip of a mouth is opened, thereby facilitating the bonding of orthodontic attachments to the molar area. However, this type of mouth gags have the following disadvantages: firstly, the above-mentioned two types of mouth gags are complex in processing and manufacturing, and have high processing and manufacturing costs; secondly, since the main material of the mouth gags is plastics, the resistance to high temperature and high pressure of sterilization is poor, and the mouth gags are prone to embrittlement and damage; and thirdly, the adaptive size adjustment is poor according to the difference of oral cavities of patients, so the universality is poor.

In order to further solve the above-mentioned technical problems, the Chinese patent document (CN 108309215 A) discloses a metal orthodontic mouth gag, which includes an upper connecting rod, a lower connecting rod, C-shaped mouth-corner pulling rods, and two support wings of the molar area which are of the same structure and in left-right mirror image. However, this metal orthodontic mouth gag has the following problems. First, since the upper connecting rod and the lower connecting rod are connected through the left C-shaped mouth-corner pulling rod and the right C-shaped mouth-corner pulling rod, the opening size of a pulling U-shaped part must be adjusted by pliers according to the size of an oral cavity of a patient in advance; the distance between the two C-shaped mouth-corner pulling rods must also be adjusted by adjusting the opening sizes of an upper U-shaped rod and a lower U-shaped rod via pliers according to the size of the oral cavity of the patient in advance; similarly, the distances between the C-shaped rods on the two sides and the respective C-shaped mouth-corner pulling rods also need to be adjusted by adjusting the opening sizes of the upper U-shaped part and the lower U-shaped part by the pliers according to the size of the oral cavity of the patient in advance, so the operation is complicated. Second, the metal orthodontic mouth gag is placed in the oral cavity, and an upper lip is opened by only relying on the upper connecting rod and a middle upper U-shaped support rod thereon; however, the upper lip may bypass the part, which excludes the middle upper U-shaped rod, of the upper connecting rod, so upper teeth are shielded by the upper lip to a certain extent; and similarly, a lower lip is opened by only relying on the lower connecting rod and a middle lower U-shaped support rod thereon, whereas the lower lip may bypass the part, which excludes the middle lower U-shaped rod, of the lower connecting rod, so lower teeth are shielded by the lower lip to a certain extent, which is not convenient for hospital personnel to operate on the teeth of the patient.

SUMMARY

In view of the above-mentioned disadvantages in the prior art, the present disclosure provides a metal orthodontic mouth gag which can completely open the upper lip, the lower lip, and the mouth corners, and meanwhile, adjust the size according to the extrusion force of an oral cavity.

In order to solve the above-mentioned technical problems, the present disclosure adopts the following technical solutions.

A metal orthodontic mouth gag, comprising an upper support frame, a lower support frame, a support wing of a left molar area, and a support wing of a right molar area, wherein the upper support frame is a serpentine upward-bent rod formed by sequentially winding a thin steel wire up and down, and a left end and a right end of the serpentine upward-bent rod are positioned at a lowest position of the serpentine upward-bent rod; the lower support frame is a serpentine downward-bent rod formed by sequentially winding another thin steel wire up and down, and a left end and a right end of the serpentine downward-bent rod are positioned at a highest position of the serpentine downward-bent rod; the support wing of the left molar area includes a left C-shaped support rod and a left blocking support frame, the support wing of the right molar area includes a right C-shaped support rod and a right blocking support frame; an upper end of the left C-shaped support rod is connected to the left end of the serpentine upward-bent rod through a first connecting rod, a lower end of the left C-shaped support rod is connected to the left end of the serpentine downward-bent rod through a second connecting rod, an upper end of the right C-shaped support rod is connected to the right end of the serpentine upward-bent rod through a third connecting rod, and a lower end of the right C-shaped support rod is connected to the right end of the serpentine downward-bent rod through a fourth connecting rod; the left C-shaped support rod, the first connecting rod, the second connecting rod, the serpentine upward-bent rod, the serpentine downward-bent rod, the third connecting rod, the fourth connecting rod, and the right C-shaped support rod are combined together to form an arc shape that is in contact with a periphery of teeth in an oral cavity; the left blocking support frame includes a first left strut, a second left strut, and a left arched rod; one end of the first left strut is arranged on an inner side of the left C-shaped support rod and is close to an upper part of the left C-shaped support rod, and one end of the second left strut is arranged on the inner side of the left C-shaped support rod and is close to a lower part of the left C-shaped support rod; an other end of the first left strut extends toward the left end of the serpentine upward-bent rod, and an other end of the second left strut extends toward the left end of the serpentine upward-bent rod; two ends of the left arched rod are respectively connected to the other end of the first left strut and the other end of the second left strut, and a middle part of the left arched rod arches outwards; the right blocking support frame includes a first right strut, a second right strut, and a right arched rod; one end of the first right strut is arranged on an inner side of the right C-shaped support rod and is close to an upper part of the right C-shaped support rod, and one end of the second right strut is arranged on the inner side of the right C-shaped support rod and is close to a lower part of the right C-shaped support rod; an other end of the first right strut extends toward the right end of the serpentine upward-bent rod, and an other end of the second right strut extends toward the right end of the serpentine upward-bent rod; two ends of the right arched rod are respectively connected to the other end of the first right strut and the other end of the second right strut, and a middle part of the right arched rod arches outwards.

As a preferred solution of the present disclosure, the serpentine upward-bent rod includes upward-bent-rod lower sections and upward-bent-rod upper sections; an end of each of the upward-bent-rod lower section which is connected to a corresponding one of the upward-bent-rod upper sections is obliquely arranged outwards and upwards; each of the upward-bent-rod lower sections forms an included angle of 10 to 20° with a horizontal plane; and an end of each of the upward-bent-rod upper sections which is away from a corresponding one the upward-bent-rod lower sections is obliquely arranged outwards and upwards, and forms an angle of 110 to 150° with the corresponding one of the upward-bent-rod lower sections; the serpentine downward-bent rod includes downward-bent-rod upper sections and downward-bent-rod lower sections; an end of each of the upward-bent-rod upper sections which is connected to a corresponding one of the downward-bent-rod lower sections is obliquely arranged outwards and upwards; each of the downward-bent-rod upper sections forms an included angle of 10 to 20° with the horizontal plane; and an end of each of the upward-bent-rod lower sections which is away from a corresponding one of the downward-bent-rod upper sections is obliquely arranged outwards and upwards, and forms an angle of 110 to 150° with the corresponding one of the downward-bent-rod upper section.

As another preferred solution of the present disclosure, lengths of both the serpentine upward-bent rod and the serpentine downward-bent rod each range from 53 mm to 73 mm; a distance between an outwardly arching section of the middle part of the left arched rod and a leftmost end of the left C-shaped support rod ranges from 25 mm to 35 mm; a distance between the outwardly arching section of the middle part of the right arched rod and a rightmost end of the right C-shaped support rod ranges from 25 mm to 35 mm; and a distance between the serpentine upward-bent rod and the serpentine downward-bent rod ranges from 27 mm to 37 mm.

As an improved solution of the present disclosure, a vertical height of each of the upward-bent-rod upper sections ranges from 6 mm to 7 mm, a horizontal width of each of the upward-bent-rod lower sections is 5 mm, and a distance between adjacent two of the upward-bent-rod upper sections of the serpentine upward-bent rod ranges from 7 mm to 8 mm; and a vertical height of each of the downward-bent-rod lower sections ranges from 6 mm to 7 mm, a horizontal width of each of the downward-bent-rod upper sections is 5 mm, and a distance between adjacent two of the downward-bent-rod upper sections of the serpentine downward-bent rod ranges from 7 mm to 8 mm.

As another improved solution of the present disclosure, the left C-shaped support rod, the first connecting rod, the second connecting rod, the serpentine upward-bent rod, the serpentine downward-bent rod, the third connecting rod, the fourth connecting rod, and the right C-shaped support rod are integrally formed.

As a further improved solution of the present disclosure, the first left strut, the second left strut, and the left arched rod are integrally formed, and the first right strut, the second right strut, and the right arched rod are integrally formed.

Compared with the prior art, the present disclosure has the following advantages.

1. The upper support frame is a serpentine upward-bent rod formed by sequentially winding a thin steel wire up and down, and the lower support frame is a serpentine downward-bent rod formed by sequentially winding a thin steel wire up and down. So, the serpentine upward-bent rod and the serpentine downward-bent rod have certain elasticity in the left-right direction. The left blocking support frame is connected to the interior of the left C-shaped support rod, and the right blocking support frame is connected to the interior of the right C-shaped support rod. The serpentine upward-bent rod and the serpentine downward-bent rod are only connected at two ends of each of the C-shaped support rods. The left blocking support frame and the right blocking support frame are not connected to the upper support frame and the lower support frame, and the left blocking support frame and the right blocking support frame do not restrain the elastic force between the serpentine upward-bent rod and the serpentine downward-bent rod in the up-down direction. So, the distance between the serpentine upward-bent rod and the serpentine downward-bent rod can be adjusted. The length and the width of the mouth gag can be adjusted according to the pressure applied to the mouth gag by an oral cavity of a patient, after the metal orthodontic mouth gag is in contact with the periphery of teeth in the oral cavity, so the universality is higher.

2. After the metal orthodontic mouth gag is in contact with the periphery of the teeth in the oral cavity, the upper lip and the lower lip are completely opened by the serpentine upward-bent rod and serpentine downward-bent rod; and the mouth corners on the left side and the right side are opened by the left arched rod and the right arched rod, and are prevented from sliding to the middle. So the whole teeth are completely exposed.

Figure 1:
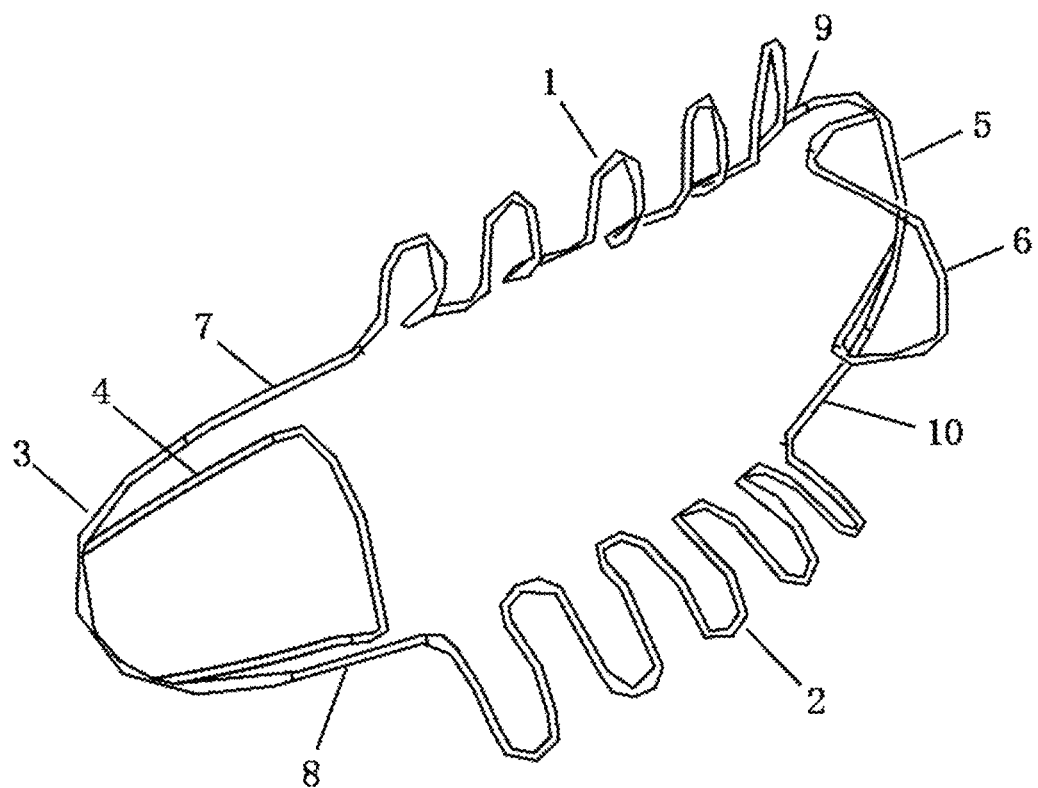
FIG. 1 is a schematic structural diagram of a metal orthodontic mouth gag.

Reference signs in the drawings: 1—serpentine upward-bent rod; 2—serpentine downward-bent rod; 3—left C-shaped support rod; 4—left blocking support frame; 5—right C-shaped support rod; 6—right blocking support frame; 7—first connecting rod; 8—second connecting rod; 9—third connecting rod; 10—fourth connecting rod; 11—first left strut; 12—second left strut; 13—left arched rod; 14—first right strut; 15—second right strut; 16—right arched rod; 17—upward-bent-rod lower section; 18—upward-bent-rod upper section; 19—downward-bent-rod upper section; and 20—downward-bent-rod lower section.

DETAILED DESCRIPTION OF THE EMBODIMENTS

The present disclosure will be further described in detail below with reference to the drawings and specific implementation manners.

As shown in FIG. 1, a metal orthodontic mouth gag includes an upper support frame, a lower support frame, a support wing of a left molar area, and a support wing of a right molar area.

The upper support frame is a serpentine upward-bent rod 1 formed by sequentially winding a thin steel wire up and down, and both the left end and the right end of the serpentine upward-bent rod 1 are positioned at the lowest position of the serpentine upward-bent rod 1. The lower support frame is a serpentine downward-bent rod 2 formed by sequentially winding a thin steel wire up and down, and both the left end and the right end of the serpentine downward-bent rod 2 are positioned at the highest position of the serpentine downward-bent rod 2. The lengths of the serpentine upward-bent rod 1 and the serpentine downward-bent rod 2 can elongated and shortened when the serpentine upward-bent rod 1 and the serpentine downward-bent rod 2 are pulled or pressed in the left-right direction.

The support wing of the left molar area includes a left C-shaped support rod 3 and a left blocking support frame 4, and the support wing of the right molar area includes a right C-shaped support rod 5 and a right blocking support frame 6. The upper end of the left C-shaped support rod 3 is connected to the left end of the serpentine upward-bent rod 1 through a first connecting rod 7. The lower end of the left C-shaped support rod 3 is connected to the left end of the serpentine downward-bent rod 2 through a second connecting rod 8. The upper end of the right C-shaped support rod 5 is connected to the right end of the serpentine upward-bent rod 1 through a third connecting rod 9, and the lower end of the right C-shaped support rod 5 is connected to the right end of the serpentine downward-bent rod 2 through a fourth connecting rod 10. The left C-shaped support rod 3, the first connecting rod 7, the second connecting rod 8, the serpentine upward-bent rod 1, the serpentine downward-bent rod 2, the third connecting rod 9, the fourth connecting rod 10, and the right C-shaped support rod 5 are combined to form an arc shape that can be in contact with the periphery of teeth in the oral cavity. After the metal orthodontic mouth gag is in contact with the periphery of the teeth in the oral cavity, an upper lip is supported by the serpentine upward-bent rod 1, and a lower lip is supported by the serpentine upward-bent rod 2, so that the lips are prevented from being in contact with the teeth.

Figure 2:
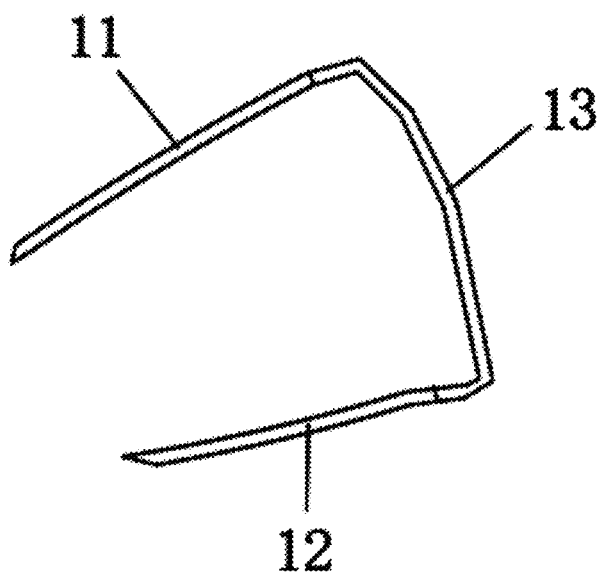
FIG. 2 is a schematic structural diagram of a left blocking support frame.
Figure 3:
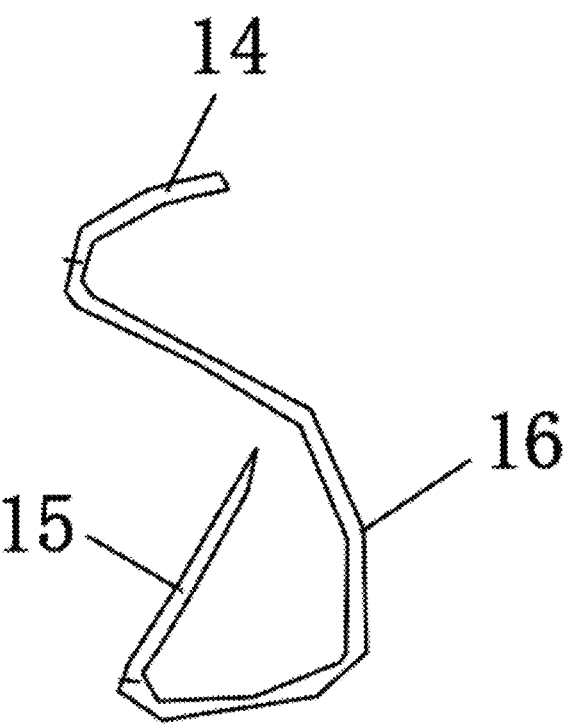
FIG. 3 is a schematic structural diagram of a right blocking support frame.

The left blocking support frame 4 includes a first left strut 11, a second left strut 12, and a left arched rod 13. As shown in FIG. 2, the left end of the first left strut 11 is arranged on the inner side of the left C-shaped support rod 3 and is close to an upper part of the left C-shaped support rod, and the left end of the second left strut 12 is arranged on the inner side of the left C-shaped support rod 3 and is close to a lower part of the left C-shaped support rod. The right end of the first left strut 11 extends towards the left end of the serpentine upward-bent rod 1, and the right end of the second left strut 12 extends towards the left end of the serpentine upward-bent rod 2. Two ends of the left arched rod 13 are respectively connected to the right ends of both the first left strut 11 and the second left strut 12, and the middle part of the left arched rod 13 arches outwards. The right blocking support frame 6 includes a first right strut 14, a second right strut 15, and a right arched rod 16. As shown in FIG. 3, the right end of the first right strut 14 is arranged on the inner side of the right C-shaped support rod 5 and is close to an upper part of the right C-shaped support rod, and the right end of the second right strut 15 is arranged on the inner side of the right C-shaped support rod 5 and is close to a lower part of the right C-shaped support rod. The left end of the first right strut 14 extends towards the right end of the serpentine upward-bent rod 1, and the left end of the second right strut 15 extends towards the right end of the serpentine upward-bent rod 2. Two ends of the right arched rod 16 are respectively connected to the left ends of both the first right strut 14 and the second right strut 15, and the middle part of the right arched rod 16 arches outwards. After the metal orthodontic gag is in contact with the periphery of the teeth in the oral cavity, the mouth corners on the left side and the right side are opened by the left arched rod 13 and the right arched rod 16, and the lips on the two sides are prevented from sliding inwards, so that the whole teeth are completely exposed.

Figure 4:
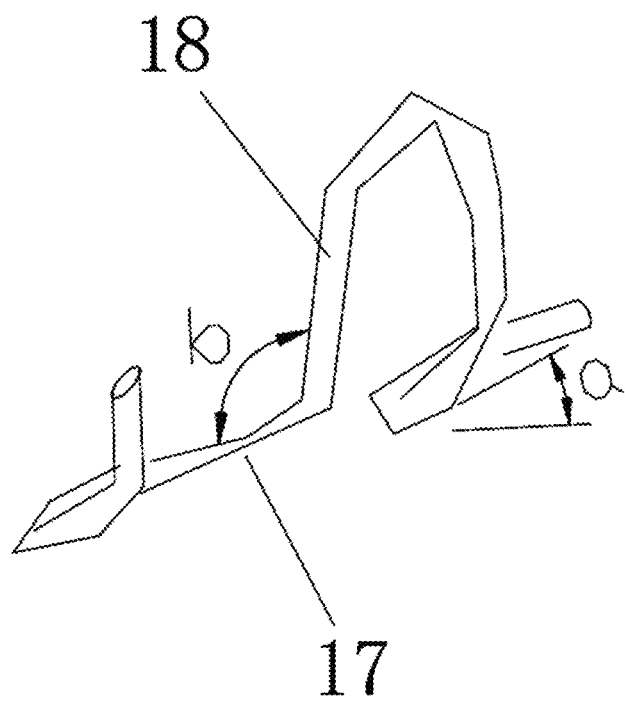
FIG. 4 is a partial schematic structural diagram of a serpentine upward-bent rod.
Figure 5:
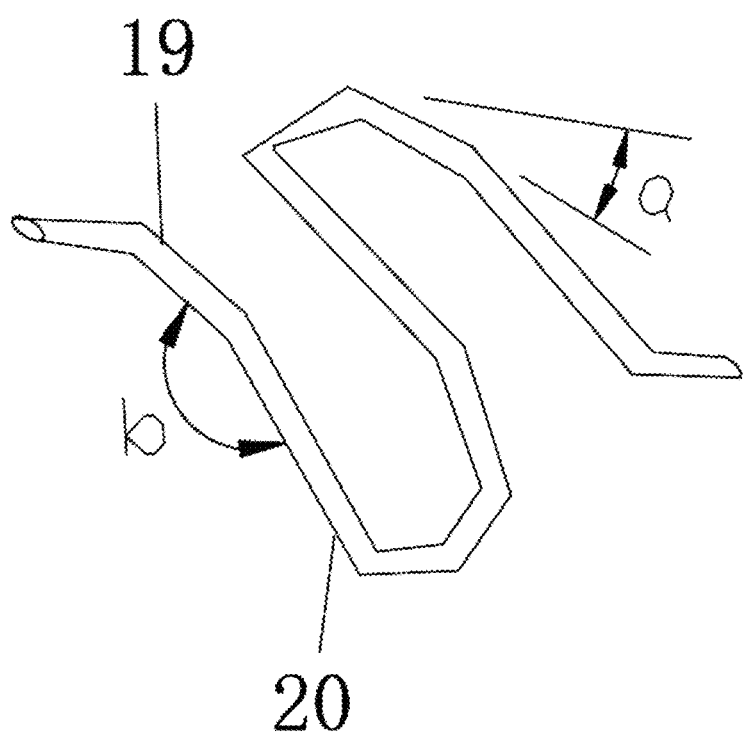
FIG. 5 is a partial schematic structural diagram of a serpentine downward-bent rod.

The serpentine upward-bent rod 1 includes upward-bent-rod lower sections 17 and upward-bent-rod upper sections 18, as shown in FIG. 4. An end, which is connected to the upward-bent-rod upper section 18, of the upward-bent-rod lower section 17 is obliquely arranged outwards and upwards. The upward-bent-rod lower section 17 forms an included angle of 10 to 20° with the horizontal plane, for example, and included angle a in FIG. 4. An end, which is away from the upward-bent-rod lower section 17, of the upward-bent-rod upper section 18 is obliquely arranged outwards and upwards and forms an angle of 110 to 150° with the upward-bent-rod lower section, for example, an angle b in FIG. 4. The serpentine downward-bent rod 2 includes downward-bent-rod upper sections 19 and downward-bent-rod lower sections 20, as shown in FIG. 5. An end, which is connected to the downward-bent-rod lower section 20, of the upward-bent-rod upper section 19 is obliquely arranged outwards and upwards. The downward-bent-rod upper section 19 forms an included angle of 10 to 20° with the horizontal plane, for example, an included angle a in FIG. 5. An end, which is away from the downward-bent-rod upper section 19, of the upward-bent-rod lower section 20 is obliquely arranged outwards and upwards, and forms an angle of 110 to 150° with the downward-bent-rod upper section 19, for example, an angle b in FIG. 5. The two types of sections of the serpentine upward-bent rod 1 are obliquely arranged outwards and upwards, so that the upper lip is further raised upwards or curled upwards when the upper lip is opened. The two types of sections of the serpentine down-bent rod 2 are obliquely arranged outwards and downwards, so that the upper lip is further raised downwards or curled downwards when the lower lip is opened. Therefore, the opening angles of the upper lip and the lower lip are larger.

The lengths of both the serpentine upward-bent rod 1 and the serpentine downward-bent rod 2 range from 53 mm to 73 mm. A distance between an outwardly arching section of the middle part of the left arched rod 13 and a leftmost end of the left C-shaped support rod 3 ranges from 25 mm to 35 mm. A distance between an outwardly arching section of the middle part of the right arched rod 16 and a rightmost end of the right C-shaped support rod 5 ranges from 25 mm to 35 mm. A distance between the serpentine upward-bent rod 1 and the serpentine downward-bent rod 2 ranges from 27 mm to 37 mm. The length and the width of the metal orthodontic mouth gag are limited to a certain range through the above-mentioned dimensions, so that the metal orthodontic mouth gag is suitable for most people to use.

A vertical height of the upward-bent-rod upper section 18 ranges from 6 mm to 7 mm, a horizontal width of the upward-bent-rod lower section 17 is 5 mm, and a distance between adjacent two of the upward-bent-rod upper sections of the serpentine upward-bent rod 1 ranges from 7 mm to 8 mm. A vertical height of the downward-bent-rod lower section 20 is 6 to 7 mm, a horizontal width of the downward-bent-rod upper section 19 is 5 mm, and a distance between adjacent two of the downward-bent-rod upper sections of the serpentine downward-bent rod 2 ranges from 7 mm to 8 mm. The vertical and horizontal widths of both the serpentine upward-bent rod 1 and the serpentine downward-bent rod 2 are limited to a certain range through the above-mentioned dimensions, so as to adapt to the thickness of the lip of the patient and make the lip reach a sufficiently large opening angle.

The left C-shaped support rod 3, the first connecting rod 7, the second connecting rod 8, the serpentine upward-bent rod 1, the serpentine downward-bent rod 2, the third connecting rod 9, the fourth connecting rod 10, and the right C-shaped support rod 5 are integrally formed. The first left strut 11, the second left strut 12, and the left arched rod 13 are integrally formed, and the first right strut 14, the second right strut 15, and the right arched rod 16 are integrally formed. The whole metal orthodontic mouth gag is made of steel wires, so that the metal orthodontic mouth gag does not only have certain strength, but also has good elasticity. The mouth gag is a metal product, so it can withstand high temperature, can be sterilizable, and can be used repeatedly.

The upper support frame of the present disclosure is a serpentine upward-bent rod 1 formed by sequentially winding a thin steel wire up and down, and the lower support frame is a serpentine downward-bent rod 2 formed by sequentially winding a thin steel wire up and down. The serpentine upward-bent rod 1 and the serpentine downward-bent rod 2 have certain elasticity in the left-right direction. The left blocking support frame 4 is connected to the interior of the left C-shaped support rod 3, and the right blocking support frame 6 is connected to the interior of the right C-shaped support rod 5. The serpentine upward-bent rod 1 and the serpentine downward-bent rod 2 are only connected at two ends of each of the left C-shaped support rod 3 and the right C-shaped support rod 5. The left blocking support frame 4 and the right blocking support frame 6 are not connected to the upper support frame and the lower support frame, and the left blocking support frame 4 and the right blocking support frame 6 do not restrain the elastic force between the serpentine upward-bent rod 1 and the serpentine downward-bent rod 2 in the up-down direction. So, the distance between the serpentine upward-bent rod 1 and the serpentine downward-bent rod 2 can be adjusted. The length and the width of the mouth gag can be adjusted according to the pressure applied to the mouth gag by an oral cavity of a patient, after the metal orthodontic mouth gag is in contact with the periphery of teeth in the oral cavity, so the universality is higher. The upper lip and the lower lip are completely opened by the serpentine upward-bent rod 1 and the serpentine downward-bent rod 2, and the mouth corners on the left side and the right side are opened by the left arched rod 13 and the right arched rod 16, and are prevented from sliding to the middle. So, the whole teeth are completely exposed.

Finally, it is noted that the above-mentioned embodiments are merely intended to illustrate rather than limit the technical solutions of the present disclosure. Although, the present disclosure is described in detail with reference to better embodiments, those of ordinary skilled in the art should understand that modifications and equivalents can be made to the technical solutions of the present disclosure without departing from the spirit and scope of the present disclosure, and all of them shall be covered by the claims of the prevent disclosure.

What is claimed is:

1. A metal orthodontic mouth gag, comprising an upper support frame, a lower support frame, a support wing of a left molar area, and a support wing of a right molar area, wherein the upper support frame is a serpentine upward-bent rod formed by sequentially winding a thin steel wire up and down, and a left end and a right end of the serpentine upward-bent rod are positioned at a lowest position of the serpentine upward-bent rod; the lower support frame is a serpentine downward-bent rod formed by sequentially winding another thin steel wire up and down, and a left end and a right end of the serpentine downward-bent rod are positioned at a highest position of the serpentine downward-bent rod;

the support wing of the left molar area comprises a left C-shaped support rod and a left blocking support frame, the support wing of the right molar area comprises a right C-shaped support rod and a right blocking support frame; an upper end of the left C-shaped support rod is connected to the left end of the serpentine upward-bent rod through a first connecting rod, a lower end of the left C-shaped support rod is connected to the left end of the serpentine downward-bent rod through a second connecting rod, an upper end of the right C-shaped support rod is connected to the right end of the serpentine upward-bent rod through a third connecting rod, and a lower end of the right C-shaped support rod is connected to the right end of the serpentine downward-bent rod through a fourth connecting rod; the left C-shaped support rod, the first connecting rod, the second connecting rod, the serpentine upward-bent rod, the serpentine downward-bent rod, the third connecting rod, the fourth connecting rod, and the right C-shaped support rod are combined together to form an arc shape that is in contact with a periphery of teeth in an oral cavity;

the left blocking support frame comprises a first left strut, a second left strut, and a left arched rod; one end of the first left strut is arranged on an inner side of the left C-shaped support rod and is close to an upper part of the left C-shaped support rod, and one end of the second left strut is arranged on the inner side of the left C-shaped support rod and is close to a lower part of the left C-shaped support rod; an other end of the first left strut extends toward the left end of the serpentine upward-bent rod, and an other end of the second left strut extends toward the left end of the serpentine upward-bent rod; two ends of the left arched rod are respectively connected to the other end of the first left strut and the other end of the second left strut, and a middle part of the left arched rod arches outwards; the right blocking support frame comprises a first right strut, a second right strut, and a right arched rod; one end of the first right strut is arranged on an inner side of the right C-shaped support rod and is close to an upper part of the right C-shaped support rod, and one end of the second right strut is arranged on the inner side of the right C-shaped support rod and is close to a lower part of the right C-shaped support rod; an other end of the first right strut extends toward the right end of the serpentine upward-bent rod, and an other end of the second right strut extends toward the right end of the serpentine upward-bent rod; two ends of the right arched rod are respectively connected to the other end of the first right strut and the other end of the second right strut, and a middle part of the right arched rod arches outwards.

2. The metal orthodontic mouth gag according to claim 1, wherein the serpentine upward-bent rod comprises upward-bent-rod lower sections and upward-bent-rod upper sections; an end of each of the upward-bent-rod lower section which is connected to a corresponding one of the upward-bent-rod upper sections is obliquely arranged outwards and upwards; each of the upward-bent-rod lower sections forms an included angle of 10 to 20° with a horizontal plane; and an end of each of the upward-bent-rod upper sections which is away from a corresponding one the upward-bent-rod lower sections is obliquely arranged outwards and upwards, and forms an angle of 110 to 150° with the corresponding one of the upward-bent-rod lower sections; the serpentine downward-bent rod comprises downward-bent-rod upper sections and downward-bent-rod lower sections; an end of each of the upward-bent-rod upper sections which is connected to a corresponding one of the downward-bent-rod lower sections is obliquely arranged outwards and upwards; each of the downward-bent-rod upper sections forms an included angle of 10 to 20° with the horizontal plane; and an end of each of the upward-bent-rod lower sections which is away from a corresponding one of the downward-bent-rod upper sections is obliquely arranged outwards and upwards, and forms an angle of 110 to 150° with the corresponding one of the downward-bent-rod upper sections.

3. The metal orthodontic mouth gag according to claim 2, wherein a vertical height of each of the upward-bent-rod upper sections ranges from 6 mm to 7 mm, a horizontal width of each of the upward-bent-rod lower sections is 5 mm, and a distance between adjacent two of the upward-bent-rod upper sections of the serpentine upward-bent rod ranges from 7 mm to 8 mm; and a vertical height of each of the downward-bent-rod lower sections ranges from 6 mm to 7 mm, a horizontal width of each of the downward-bent-rod upper sections is 5 mm, and a distance between adjacent two of the downward-bent-rod upper sections of the serpentine downward-bent rod ranges from 7 mm to 8 mm.

4. The metal orthodontic mouth gag according to claim 3, wherein the left C-shaped support rod, the first connecting rod, the second connecting rod, the serpentine upward-bent rod, the serpentine downward-bent rod, the third connecting rod, the fourth connecting rod, and the right C-shaped support rod are integrally formed.

5. The metal orthodontic mouth gag according to claim 4, wherein the first left strut, the second left strut, and the left arched rod are integrally formed, and the first right strut, the second right strut, and the right arched rod are integrally formed.

6. The metal orthodontic mouth gag according to claim 2, wherein the left C-shaped support rod, the first connecting rod, the second connecting rod, the serpentine upward-bent rod, the serpentine downward-bent rod, the third connecting rod, the fourth connecting rod, and the right C-shaped support rod are integrally formed.

7. The metal orthodontic mouth gag according to claim 6, wherein the first left strut, the second left strut, and the left arched rod are integrally formed, and the first right strut, the second right strut, and the right arched rod are integrally formed.

8. The metal orthodontic mouth gag according to claim 1, wherein lengths of both the serpentine upward-bent rod and the serpentine downward-bent rod each range from 53 mm to 73 mm; a distance between an outwardly arching section of the middle part of the left arched rod and a leftmost end of the left C-shaped support rod ranges from 25 mm to 35 mm; a distance between the outwardly arching section of the middle part of the right arched rod and a rightmost end of the right C-shaped support rod ranges from 25 mm to 35 mm; and a distance between the serpentine upward-bent rod and the serpentine downward-bent rod ranges from 27 mm to 37 mm.

9. The metal orthodontic mouth gag according to claim 8, wherein the left C-shaped support rod, the first connecting rod, the second connecting rod, the serpentine upward-bent rod, the serpentine downward-bent rod, the third connecting rod, the fourth connecting rod, and the right C-shaped support rod are integrally formed.

10. The metal orthodontic mouth gag according to claim 9, wherein the first left strut, the second left strut, and the left arched rod are integrally formed, and the first right strut, the second right strut, and the right arched rod are integrally formed.

11. The metal orthodontic mouth gag according to claim 1, wherein the left C-shaped support rod, the first connecting rod, the second connecting rod, the serpentine upward-bent rod, the serpentine downward-bent rod, the third connecting rod, the fourth connecting rod, and the right C-shaped support rod are integrally formed.

12. The metal orthodontic mouth gag according to claim 11, wherein the first left strut, the second left strut, and the left arched rod are integrally formed, and the first right strut, the second right strut, and the right arched rod are integrally formed.

* * * * *